(12) United States Patent
Korten et al.

(10) Patent No.: US 10,028,810 B2
(45) Date of Patent: Jul. 24, 2018

(54) METHOD OF CAPTURING DATA FROM A PATIENT'S DENTITION AND SYSTEM FOR PERFORMING SUCH METHOD

(71) Applicant: 3M INNOVATIVE PROPERTIES COMPANY, St. Paul, MN (US)

(72) Inventors: Malte Korten, Moorenweis (DE); Helmar B. Mayr, Kaufering (DE); Gallus Schechner, Hersching (DE); Gioacchino Raia, Turkenfeld (DE)

(73) Assignee: 3M Innovative Properties Company, St. Paul, MN (US)

( * ) Notice: Subject to any disclaimer, the term of this patent is extended or adjusted under 35 U.S.C. 154(b) by 96 days.

(21) Appl. No.: 14/785,432

(22) PCT Filed: Apr. 24, 2014

(86) PCT No.: PCT/US2014/035227
§ 371 (c)(1),
(2) Date: Oct. 19, 2015

(87) PCT Pub. No.: WO2014/179141
PCT Pub. Date: Nov. 6, 2014

(65) Prior Publication Data
US 2016/0067018 A1    Mar. 10, 2016

(30) Foreign Application Priority Data
Apr. 29, 2013    (EP) .................................... 13165808

(51) Int. Cl.
*A61C 13/08*    (2006.01)
*A61C 9/00*    (2006.01)
(Continued)

(52) U.S. Cl.
CPC ............ *A61C 13/082* (2013.01); *A61B 1/051* (2013.01); *A61B 1/24* (2013.01); *A61C 9/0053* (2013.01); *A61C 13/34* (2013.01); *G01J 3/508* (2013.01)

(58) Field of Classification Search
CPC ... A61C 13/082; A61C 13/0004; A61C 13/34; A61C 9/0053; A61C 1/051; A61C 1/24; G01J 3/508
(Continued)

(56) References Cited

U.S. PATENT DOCUMENTS 7,234,937 B2 *    6/2007    Sachdeva ................. A61C 7/00
                                                                        433/24
2009/0168063 A1    7/2009    Kobayashi
2012/0015316 A1 *    1/2012    Sachdeva ............. A61C 19/045
                                                                        433/24

FOREIGN PATENT DOCUMENTS

CN    200945199    9/2007
EP    1607041    12/2005
(Continued)

OTHER PUBLICATIONS

International Search Report for PCT International Application No. PCT/US2014/035227 dated Aug. 11, 2014, 4 pages.

*Primary Examiner* — Ralph Lewis

(57) ABSTRACT

A method of capturing data from a patient's dentition with the steps of positioning a first optical sensor relative to patient's dentition, capturing the shape of a tooth in the patient's dentition, independent from capturing the shape, measuring a color at a location on the tooth, and providing a correlation between the location of the color and a coordinate in the captured shape. The invention helps providing a dental restoration at a relatively high optical, mechanical, and geometric quality.

14 Claims, 3 Drawing Sheets

(51) Int. Cl.
*G01J 3/50* (2006.01)
*A61B 1/05* (2006.01)
*A61B 1/24* (2006.01)
*A61C 13/34* (2006.01)

(58) Field of Classification Search
USPC .......................................................... 433/29
See application file for complete search history.

(56) References Cited

FOREIGN PATENT DOCUMENTS

| | | | |
|---|---|---|---|
| EP | 1607041 A2 * | 12/2005 | ......... A61B 1/00009 |
| WO | WO 2001-80761 | 11/2001 | |
| WO | WO 0180761 A2 * | 11/2001 | ............... A61C 7/00 |
| WO | WO 2004-004554 | 1/2004 | |
| WO | WO 2012-007003 | 1/2012 | |
| WO | WO 2012007003 A1 * | 1/2012 | ............. A61C 9/004 |
| WO | WO 2012-078533 | 6/2012 | |
| WO | WO 2012/083967 | 6/2012 | |
| WO | WO 2013-095968 | 6/2013 | |

\* cited by examiner

METHOD OF CAPTURING DATA FROM A PATIENT'S DENTITION AND SYSTEM FOR PERFORMING SUCH METHOD

FIELD OF THE INVENTION

The invention relates to a method and a system for capturing a shape and for measuring a color from a patient's dentition. In particular the invention relates to a method and a system which allows for capturing the shape and for measuring the color in independent steps and for providing a correlation between the captured shape and the location at which the color is measured.

BACKGROUND ART

In the field of dentistry, the restoration of a patient's tooth or teeth generally includes the replacement of the natural tooth substance by an artificial substance. For larger restorations, pre-finished dental restorations or prostheses are commonly used to replace the tooth or teeth or at least part of those.

Ceramic materials are widely used for making high-quality dental restorations because of their good physical, aesthetic and biological properties. These restorations are often manufactured in automated processes, which typically include the use of computer-aided design (CAD) techniques and manufacturing by Computer Numerical Controlled (CNC) machines.

In the manufacturing of dental restorations various automated processes are established in practice. One common method includes the preparation of standardized blanks that subsequently can be used to machine individual dental restorations or precursors thereof by removing material from the blank. Except for providing such blank at a sufficient size suiting for a multiplicity of different types of dental restorations, the shape of the blank typically does not correlate with any individual shape of a tooth in patient's mouth.

While such processes provide various advantages meanwhile so-called build-up processes have been proposed for making dental restorations. Such a build-up process typically allows building up an individual dental restoration in substantially its desired individual shape, generally by subsequently adding material to create that shape instead of providing an oversized standardized blank from which material is removed in a subsequent process.

For example WO 2012/078533 describes such a build-up process and corresponding devices for making a dental restoration from a powdery ceramic material. Restorations manufactured by use of automated processes are often finished, for example by a dental technician, by coloring and/or glazing to make the restoration pleasantly fit with other teeth in the patient's mouth. Co-pending international patent application PCT/US2012/068724 further describes a method and system for providing a dental restoration with an individual color within an automated manufacturing process.

Although existing processes for making dental restoration are advantageous in different respects there is a general desire to provide a process for making individual or customized dental restorations at a high degree of automation, maximized quality and minimized costs.

SUMMARY OF THE INVENTION

The invention in one aspect relates to a method of capturing data from a patient's dentition. The method comprises the steps of:

positioning a first optical sensor relative to patient's dentition;

capturing via the first optical sensor at least a portion of the shape of a tooth in the patient's dentition and based thereon providing a first virtual dentition model representing that shape in a three-dimensional coordinate system;

independent from capturing the shape, measuring a first color at a first location on the tooth portion; and providing a correlation between the first location of the first color and a coordinate in the first virtual dentition model.

The invention is advantageous in that it provides for relatively precise color measuring and an association between measured colors and the location of these colors at a patient's tooth. Thus manual documentation of such association may not be necessary. Further the invention is advantageous in that it helps designing and manufacturing of aesthetically pleasant dental restorations. For example the invention may help providing a dental restoration with multiple colors which substantially match with colors of adjacent teeth in an automated process. The invention may further help minimizing errors in color measurement. In particular the invention preferably allows measuring color and accounting for translucency and reflectivity of the tooth at which the color is measured. Further although generally referred to as "color" herein, the measurement of the color may involve determination of a color according to a color scheme, like RGB, L*a*b or VITAPAN™, and additionally the determination of a translucency and/or a reflectivity.

In one embodiment the method comprises the step of positioning a second optical sensor relative to the patient's dentition. In this embodiment the measuring of the first color is performed via the second optical sensor. The positioning of the first and/or second optical sensor may be performed indirectly, for example by positioning an end of a light guide to the patient's dentition, which other end is optically coupled with the first and/or second sensor, respectively. Further the positioning of the first and/or second optical sensor may be performed directly, for example by positioning the sensor to the patient's dentition. The second sensor preferably forms at least part of a spectrometer.

Such a spectrometer preferably comprises a multiplicity of different color filters that are used in combination with a multiplicity of light sensors arranged behind such filters respectively. Each light sensor typically measures the intensity of light passing through the light filter and arriving at the light sensor. Preferably the spectrometer comprises more than 3 different color filters. In contrast to an RGB camera based on three different color filters for measuring three different colors, the spectrometer of the invention preferably allows measuring of more than three colors. In a preferred embodiment the spectrometer of the invention is configured for measuring at least 8, preferably at least 15 different colors. Therefore the spectrometer may comprise at least 8 or at least 15, 30 or 60 different color filters. Each of the color filters may be adapted to transmit light within a certain wavelength spectrum and block light outside the specified wavelength spectrum. Such filters are also referred to as "bandpass filters", and accordingly the mentioned wavelength spectrum is further referred to as "passband". Further each passband typically has a certain "bandpath width", which characterizes the size of the spectrum at which the filter is transmissive. Each of the color filters may have a passband width within a range of 5 nm (nanometers) to 40 nm, more preferably within a range of 5 nm to 25 nm, most preferably within a range of 5 nm to 10 nm. Bandpass filters are available in many different configurations, including many different bandpass widths and spectra. The skilled person will recognize that a spectrometer can likewise be provided by use of so-called band-stop filters, although bandpass filters are preferred herein.

The multiplicity of different color filters may be adapted such that the filters have their passbands within the spectrum of ultraviolet (UV) and/or visible light. For the purpose of the present specification "visible light" is defined as light within a spectrum of between 380 nm to 750 nm, and "UV light" is defined as light within a spectrum of between 315 nm to less than 380 nm. The multiplicity of different color filters of the spectrometer may be adapted such that their passbands do not overlap, in particular such that their passbands are consecutively graded within the UV and visible light spectrum. A consecutive grading may or may not comprise gaps between different passbands.

In one embodiment the passbands are consecutively graded, starting from about 315 nm to about 720 nm. Thus based on filters having for example a passband width of 10 nm, an amount of 40 different filters could substantially cover the entire spectrum between 315 and 720 nm. The skilled person will recognize that small gaps between the individual passbands (in the example in total amounting to 5 nm not covered) are desired to achieve a reliable color distinction.

The spectrometer is preferably further adapted to determine color effects from fluorescence of the measured object via measuring the UV light spectrum. In particular the spectrometer may be adapted to measure fluorescence. In this embodiment a light source having a light spectrum over a range of UV-light to visible light is provided (for example a halogen lamp). The measurement of flourescense is preferably performed by the steps of:

illuminating a tooth in the patient's mouth by the light source at the light spectrum of the light source, and simultaneously conducting a first measurement of the color at a location on that tooth which is illuminated by the light source;

providing a filter (for example a band-stop filter) which blocks UV light;

illuminating a tooth in the patient's mouth by the same light source but at a light spectrum which is reduced by the UV portion via the filter, and simultaneously conducting a second measurement of the color at the same location on that tooth.

The first measurement is thus conducted at an illumination at a first emission spectrum $S(\ )_{UV\ incl}$, whereas the second measurement is conducted at an illumination at a second emission spectrum $(S(\ )_{UV\ excl}$. The first measurement accordingly is based on capturing the remittance spectrum $R(\ )_{UV\ incl}$, whereas the second measurement is based on capturing the remittance spectrum $R(\ )_{UV\ excl}$.

The fluorescence can be determined by a subtraction of the remittance spectra $R(\ )_{Fl} = R(\ )_{UV\ incl} - R(\ )_{UV\ excl}$. The resulting differential spectrum $R(\ )_{Fl}$ corresponds to the fluorescence spectrum. The person skilled in the art will understand that the emission spectrum as well as the remittance spectrum may be measured in the form of an area formed under a curve the emission and remittance spectrum, respectively.

The actual fluorescence may correspond to a so-called radiance factor calculated from a ratio of the remittance spectrum to the emission spectrum in percent, for example:

fluorescence $\%_{(abs)} = R(\ )_{Fl}/S(\ )_{UV\ incl}$ or fluorescence $\%_{(rel)} = R(\ )_{Fl}/(S(\ )_{UV\ incl} - S(\ )_{UV\ excl})$ The term "fluorescence $\%_{(abs)}$" thereby refers to the fluorescence based on the first emission spectrum, whereas the term "fluorescence $\%_{(rel)}$" refers to the fluorescence based on the UV portion of the first emission spectrum only.

The fluorescence spectra can further be used to determine the tristimulus values X, Y and Z, which further may be used to determine other color values, like for example L*, a* and b*.

In one embodiment the second sensor is positioned at the patient's dentition for measuring a color at an angle of between about 0 degrees to 45 degrees relative to an axis perpendicular onto the surface measured.

In a further embodiment the positioning of the first sensor and the second sensor is performed simultaneously or at least over a period of time simultaneously. Thus the first color may be measured simultaneously with capturing of the shape, although the capturing of the shape and the measuring of the color are otherwise performed independent from each other. The independency of the capturing of the shape and the measuring of the color may for example be provided by the first and second sensor being based on different technical principles as described herein.

In a further embodiment the capturing of the shape involves processing of a series of bit map images and creating the first virtual dentition model based on the images. For example the capturing of the shape may be performed using a LAVA™ Chairside Oral Scanner C.O.S. or a 3M™ True Definition Scanner available from 3M Deutschland GmbH, Germany, or a device using the same or similar technical principal. The scanner may be adapted to capture the clinical situation with so-called '3D-in-Motion' technology. Unlike current point-and-click procedures, '3D-in-Motion' technology captures continuous 3D video images. These images create a digital impression used for the fabrication of CAD/CAM dental restorations. In contrast to traditional scanning methods based on a point and-click technology the user can scan images in a move of the capturing device.

In a further embodiment the method further comprises the step of associating the first color with the at least one coordinate in the first virtual dentition model based on the correlation between the first location of the first color and the coordinate in the first virtual dentition model. The measured first color may for example be stored in the form of computer processible data in an appropriate format to define the first color. Further the at least one coordinate may be stored in an appropriate format to define a unique position in a coordinate system, for example in the format of X, Y and Z coordinates based on an origin in a Cartesian coordinate system (although recognized by the person skilled in the art, it is noted for the sake of clarity that the X, Y, and Z coordinates in the Cartesian coordinate system refer to different physical parameters than the X, Y, and Z tristimulus values). The association of the first color and the at least one coordinate may be provided data based, for example by a virtual array defining associated data fields for storing colors and their associated coordinates.

In an embodiment the method further comprises the step of comparing the measured first color with a reference color, and—depending on the degree of similarity or the match between the measured first color and the reference color—determining the validity of the measured first color. The reference color may correspond to a color measured on the same tooth previously or subsequently, for example directly previously or directly subsequently. Further the reference color may correspond to a predetermined or user-selected tooth color. A mismatch between the measured first color and the reference color may trigger a further method step of issuing an error signal or message and/or may cause skipping of the measured first color. The limits of an acceptable mismatch may be adjustable by user input.

In one embodiment the method further comprises the steps of:
  measuring a second color at a second location on the same tooth or a further tooth in the patient's dentition, the second location being different from the first location;
  in case of measuring the second color on the further tooth, capturing via the first optical sensor at least a portion of the shape of that further tooth and based thereon updating the first virtual dentition model by the shape of the further tooth; and
  providing a correlation between the second location of the second color and a further coordinate in the (updated) first virtual dentition model. Further colors may be measured on the same tooth or further teeth and the first virtual dentition model may be further updated by the shape of any further teeth. Thus the entire dentition or the entire upper or lower jaw may be captured in shape and a plurality of colors may be measured thereon. The measured colors may be mapped relative to the first virtual dentition model at coordinates which correspond to the location at the dentition.

In a further embodiment the method comprises the step of matching at least the first color with a standard color from a standard color scheme. Such a standard color scheme may for example correspond to the widely used VITAPAN™ Classical tooth color scheme which typically provides the different tooth colors: A1, A2, A3, A3.5, A4, B1, B2, B3, B4, C1, C2, C3, C4, D2, D3 and D4.

In a further embodiment the method comprises the step of visualizing the first virtual dentition model including information about the first color in geometric relation to the first virtual dentition model. The visualization may for example be provided on a computer screen, for example by a three-dimensional rendering. The method may further comprise the step of providing within the first virtual dentition model a false or true color visualization of the first color (and/or further colors) in appropriate positional relationship with the coordinate correlated with the first location. Further any true color may resemble the corresponding tooth color of a standard tooth color scheme, and any false color may correspond to a particular false color which is associated with a corresponding color in a standard color scheme. For example significantly different false colors may be used to visualize tooth colors of a tooth color scheme, like the color red for A3 and the color green for A2, for example. Thus an operator is enabled to clearly distinguish between tooth colors being only slightly different in reality.

In a further embodiment the method comprises the step of providing a second virtual dentition model of a dental restoration. Such second virtual dentition model may be provided by capturing the shape of a physical model of the patient's dentition. The second virtual dentition model may be visualized in a determined geometric relationship to the first virtual dentition model. In other words the method may comprise the steps of intra-orally capturing the patient's dentition as well as extra-orally capturing a physical model of the same patient's dentition. The method may further comprise the step of matching the first and second virtual dentition models to provide a resulting virtual dentition model. Thus inaccuracies in shape resulting from intra-oral capturing may be compensated by the matching with the second virtual dentition model provided from extra-orally scanning. The method may further comprise the step of assigning the resulting virtual restoration model the first color or a color based on the first color.

In a further embodiment the method comprises the step of manufacturing a dental restoration. The manufacturing is preferably performed using a coloring enabled process, in particular coloring enabled build-up process. Thereby the dental restoration may be provided with a color based on the first color. Such a coloring enabled build-up process may be based on powder layering and layerwise coloring as disclosed in co-pending European patent application, application no.: EP 12170470, which is incorporated by reference herein.

In a further aspect the invention relates to a system for capturing data from a patient's dentition. The system is generally adapted to perform the method of the invention. In particular the system comprises:
  a first optical sensor;
  the system being adapted by aid of the first optical sensor to capture the shape of at least a tooth portion of the patient's dentition in the form of a first virtual dentition model representing that shape in a three-dimensional coordinate system;
  the system comprising a second optical sensor being adapted to measure a first color at a first location on the tooth portion independently from capturing the shape;
  wherein the system is further adapted for providing a correlation between the first location of the first color and a coordinate in the first virtual dentition model.

In one embodiment the first optical sensor comprises a plurality of CCD and/or CMOS photo sensors. The second optical sensor may form at least part of a spectrometer, for example as specified above. In a further embodiment the first optical sensor and the second optical sensor are arranged in one handpiece. The first and second optical sensor may be arranged at a fixed geometric relationship to each other. The handpiece may comprise a first light guide forming at one end a first optical input with the other end of the first light guide being optically coupled with the first sensor. Further the handpiece may comprise a second light guide forming at one end a second optical input with the other end of the second light guide being optically coupled with the second sensor. The handpiece may further have the first and second light guide. It is noted that the first sensor may form the first optical input in an embodiment having no light guide, and the second sensor may form the second optical input in an embodiment having no light guide. The first and second optical input may be arranged at a fixed geometric relationship to each other. Accordingly the first optical sensor may be optically coupled to a first light input and the second optical sensor may by optically coupled to a second light input. The first and second light input preferably face in generally the same direction and may be located adjacent each other or one within the other.

In a further embodiment the method comprises the step of capturing the inclination of the second optical input relative to the tooth surface on which the second optical input measures the first color. The method may further comprise the step of comparing the measured inclination with a reference inclination, and—depending on the accuracy between the measured inclination and the reference inclination—determining the validity of the measured first color. The reference inclination may correspond to a predetermined or user-selected inclination. A deviation between the measured inclination and the reference inclination may trigger a further method step of issuing an error signal or message and/or may cause skipping of the measured first color. The limits of an acceptable deviation in inclination may be adjustable by user input.

In one embodiment the correlation is provided by a known, for example fixed, geometric relationship between the first and second sensor or between the first and second optical input. Such a fixed relationship may be provided by the design of the handpiece. For example for creating the first virtual dentition model the position of the optical input relative to the dentition model is typically known or derivable. The position of the second optical input may be determined by a fixed three-dimensional offset from the known or derived position of the first optical input. Thus an image captured from a certain direction and distance from the dentition may be automatically correlated with the position at which the first color is measured. Further the shape of the dentition may be captured while one or more colors are measured so that the second optical input is captured together with the dentition shape. From the captured second optical input its position may be directly calculated.

In a further embodiment the system comprises a computer and the system thus is preferably adapted to perform the method of any of the invention. The system may comprise dental computer aided design (CAD) functionality for designing a dental restoration based on the first and/or second virtual dentition model. The system may be further configured to assign the design of the dental restoration one or more colors based on the first and/or second virtual dentition model. For example the system may enable the user to adjust the color of at least a portion of the dental restoration to a particular color assigned to the first and/or second virtual dentition model. The system may further comprise a build-up device for making a dental restoration, for example a device as disclosed in co-pending European patent application, application no.: EP 12170470.

DETAILED DESCRIPTION OF THE INVENTION

Figure 1:
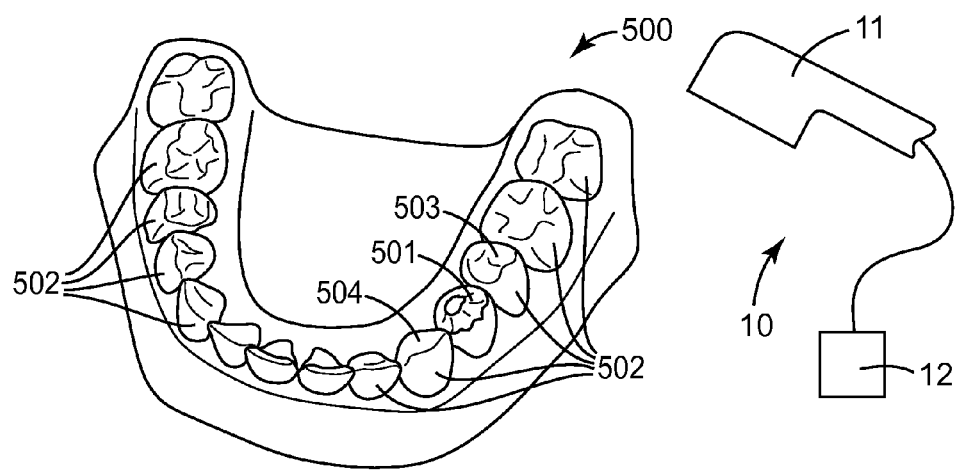
FIG. 1 is a perspective view of a patient's clinical situation in combination with a system according to an embodiment of the invention.

FIG. 1 illustrates an exemplary clinical situation in a patient's mouth. In the particular clinical situation shown the lower dentition 500 of a patient has a plurality of healthy teeth 502 and a defective tooth 501 which is prepared for restoration.

A portion of a handpiece 11 of a system 10 for capturing optical data is placed next to the patient's dentition 500. In particular the system 10 has a first optical sensor (not shown in detail in this Figure) which is thus positioned relative to patient's dentition 500. The system 10 can be used to capture via the first optical sensor the shape of one or more teeth in the patient's dentition 500. The system 10 is adapted such that it can provide—based on the captured shape—a first virtual dentition model representing that shape in a three-dimensional coordinate system. The system 10 therefore further comprises a computer 12 which has appropriate software for processing captured image data and for virtual modeling. The system 10 is further adapted to measure a color at the patient's dentition. Although not illustrated in detail the system 10 therefore may have a second optical sensor integrated in the handpiece 11 or in a further handpiece (nor shown).

The system 10 is preferably used to capture at least a portion of the shape of a tooth, for example one of the healthy teeth 502, in the patient's dentition 500 and to measure a first color at a first location on that tooth portion. Preferably the shape of a tooth (for example tooth 503 or 504) adjacent the prepared tooth 501 is captured at least partially, and the first color is additionally taken from the same adjacent tooth 503 or 504, respectively. The first color may in a separate step be used to provide a dental restoration (not shown) for the prepared tooth with a color that fits the color of the adjacent tooth or teeth (503/504). Accordingly the dental restoration may not only resemble the appearance of a natural tooth but may preferably also pleasantly fit in color to an adjacent tooth, and thus pleasantly integrate in the existing optical appearance of the patient's dentition.

Based on the captured shape a first virtual dentition model is provided which preferably represents that shape in a three-dimensional coordinate system. Thus particular locations on the tooth are represented by coordinates in the first virtual dentition model. The measurement of color, for example the first color, is performed independent from capturing the shape. This means that preferably the data from capturing the shape are not used to derive color therefrom, but that separate data about the color are measured in addition to the shape data. The shape data and color data are preferably subsequently correlated such that particular measured colors are brought in association with particular coordinates or locations in the corresponding first virtual dentition model of the tooth portions of which the color were measured. In the example thus a correlation between the first location of the first color and a coordinate in the first virtual dentition model is provided. Such a method preferably provides for precise color measuring including determination of location information of measured colors associated with the patient's dentition.

Figure 2:
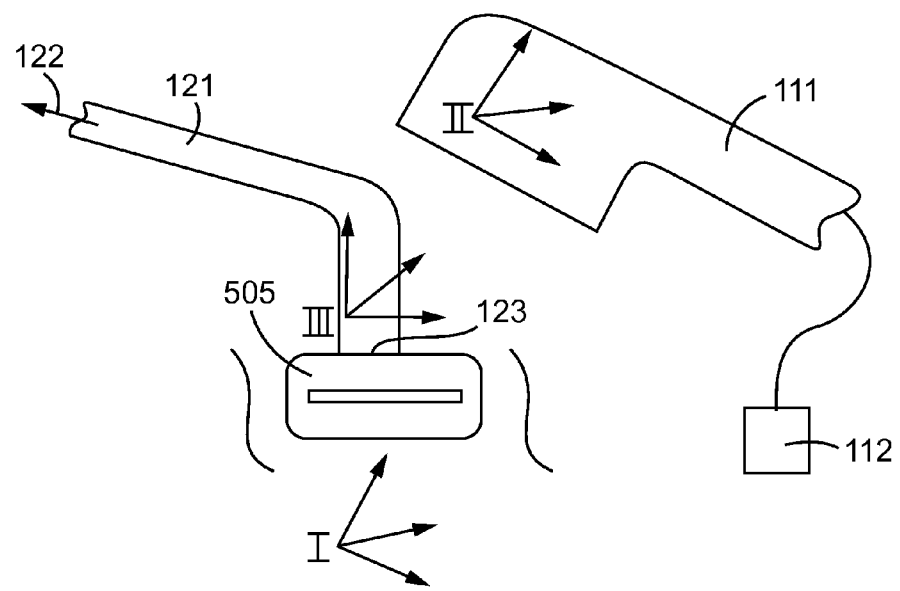
FIG. 2 is a schematic view of a system according to an embodiment of the invention.

FIG. 2 shows a first handpiece 111 for capturing shape, for example an intraoral scanner as available under the designation 3M™ True Definition Scanner from 3M Company, USA. A second handpiece 121 is provided for measuring color. Such a unit is for example available under the designation VITA Easyshade® Compact from JJL Technologies LLC, IL, USA. The first and second handpiece 111, 121 in the example are used for simultaneously capturing at least a portion of the shape of a tooth 505 and one or more colors of the same tooth, respectively. In particular the second handpiece 121 is placed on a surface of the tooth 505 for measuring a first color, while the first handpiece 111 captures part of the shape of the tooth 505. Because the second handpiece 121 is placed with its optical input 123 directly on the tooth 505, the optical input 123 is captured by the first handpiece 111 along with the tooth shape. The first and second handpiece 111, 121 are connected to a computer which is adapted to provide a first virtual dentition model from the data captured by the first handpiece 111. Further the computer is adapted to determine a first location from the position of the optical input 123 also captured by the first handpiece 111. The first location corresponds to the location at which the first color is measured so that the computer can correlate this first location of the first color to a coordinate in the first virtual dentition model. It is noted that the first handpiece 111 is preferably adapted to capture the shape on an object, for example the tooth 505, by taking a series of pictures (video sequence) of that object. Such video sequence may capture the object from different angles and thus may be used to determine the three-dimensional first virtual dentition model. Therefore the capturing of the tooth shape may be performed in at least two consecutive phases, one phase in which the tooth without the second handpiece 121 is captured and a further phase in which the tooth with the second handpiece 121 is captured. Thus the shape of the tooth area beneath the optical input 123 can also be captured.

Figure 3:
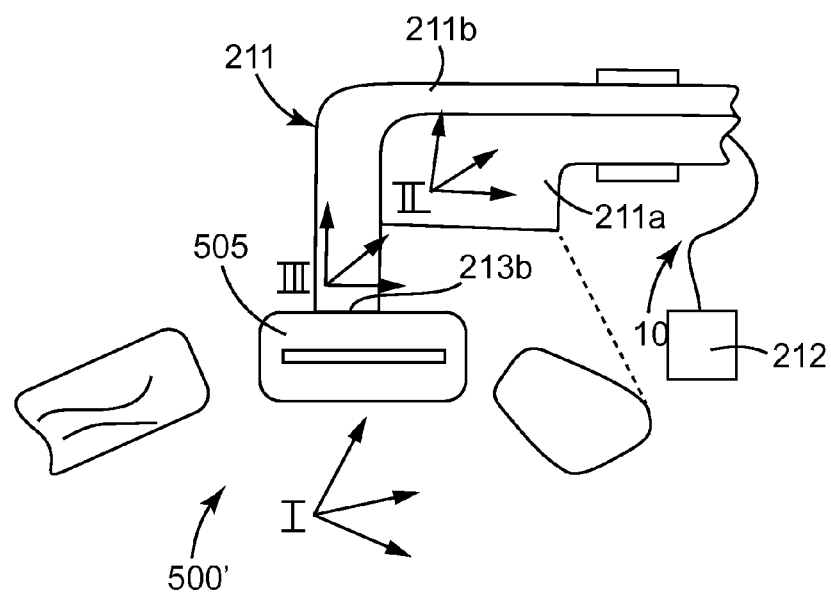
FIG. 3 is a schematic view of a system according to a further embodiment of the invention.

FIG. 3 shows a further example in which only one handpiece 211 comprises a first sensor unit 211a for shape capturing and a second sensor unit 211b for color measuring. In use, the handpiece 211 is preferably consecutively positioned at a plurality of locations on the patient's dentition 500', and a color is measured at one or more, or up to each of the plurality positions via the second sensor unit 211b. Simultaneously the first sensor unit 211a is used to capture the shape of at least a portion of the dentition by consecutively taking pictures of the dentition as the handpiece 211 is positioned to the plurality of locations. Accordingly a three-dimensional first virtual dentition model can be created from an evaluation of the pictures taken, and the plurality of measured colors may be mapped relative to coordinates in the first virtual dentition model. In this example the correlation between the location at which the color is measured and the coordinate in the first virtual dentition model can be derived from the known positional relationship of the first and second sensor unit 211a, 211b to each other. In particular the positional relationship is fixed because first and second sensor unit 211a, 211b are directly or indirectly mounted to each other. Therefore the positional relationship between the first and second sensor unit 211a, 211b (or that of their optical inputs) can be used to calculate the location at which the color is measured relative to the shape that is at the same time captured. However it is alternatively or additionally possible—similar as described in the example in FIG. 2—to derive the correlation between the location of color measuring and the coordinate in the first virtual dentition model by capturing the optical input 213b of the second sensor unit 211b along with the shape of the tooth on which the optical input 213b is placed.

Figure 4:
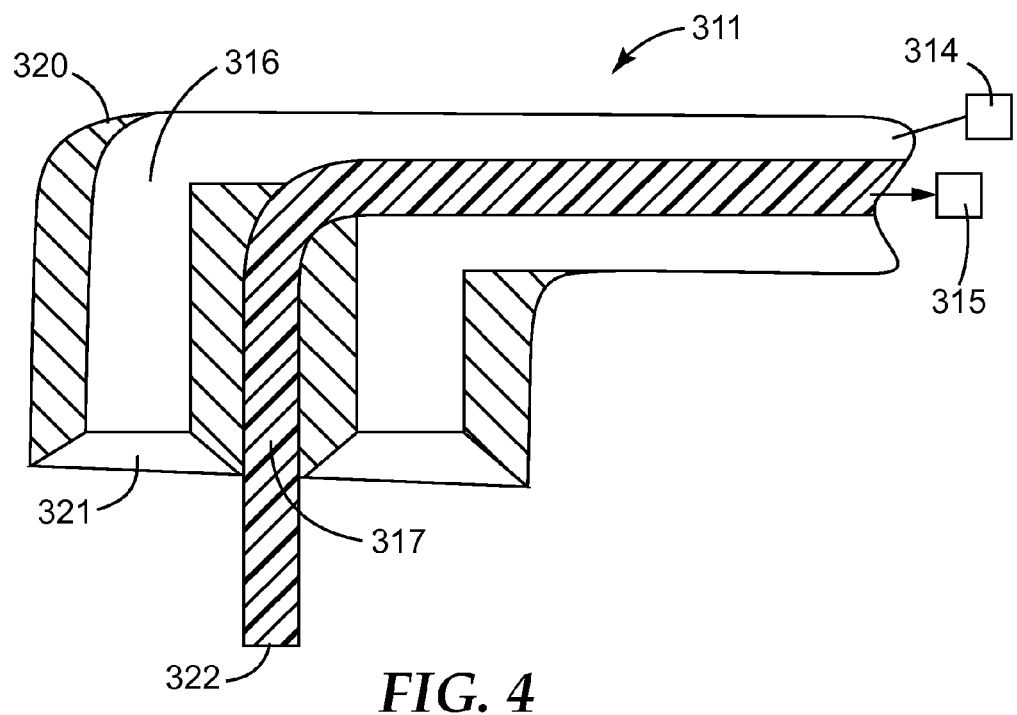
FIG. 4 is a schematic view of a system according to still a further embodiment of the invention.

FIG. 4 shows a further embodiment of a handpiece 311 in which a first optical sensor 314 for capturing shape and a second optical sensor 315 for measuring color are combined in a single device. In the example the first and second optical sensor 314, 315 are arranged adjacent respective ends of a first and second optical light guide 316, 317, respectively. The end of each light guide opposite the first and second sensor 314, 315 further form first and second optical inputs 321, 322 for the first and second sensor 314, 315, respectively. However in other embodiments at least one of the first and second optical input 314, 315 may be located directly within a head portion 320 of the handpiece 311. Such head portion 320 is preferably adapted (in particular sized and shaped) for insertion into a patient's mouth. For example the first optical input 314 may be located directly within the head portion 320 of the handpiece 311, whereas the second optical input 315 may be arranged farther away from the head portion and optically connected to the head portion 320 via the light guide 317. In such an embodiment the first optical sensor 314 may also provide the first optical input 321, whereas the light guide 317 provides the second optical input 322 for the second optical sensor 315. In the example shown the first optical input 321 surrounds the second optical input 322 and the second optical input 322 protrudes at a predetermined length beyond the first optical input 321. Thus during measuring of a color at a patient's tooth by placing the second optical input 322 on the patient's dentition the first optical input 321 is kept spaced at a predetermined distance (corresponding to the predetermined length of the protruding second optical input 322) from the patient's dentition. This helps ensuring a reliable capturing of the shape and color during a single procedure. Further the protruding second optical end 322 may be captured by the first optical sensor 314 during shape capturing and color measurement for determining the correlation between the location of the color measurement and a coordinate in the first virtual dentition model created from capturing the shape. However such correlation can also be determined by calculation based on the geometric configuration of the first and second optical input 321, 322 relative to each other.

Figure 5:
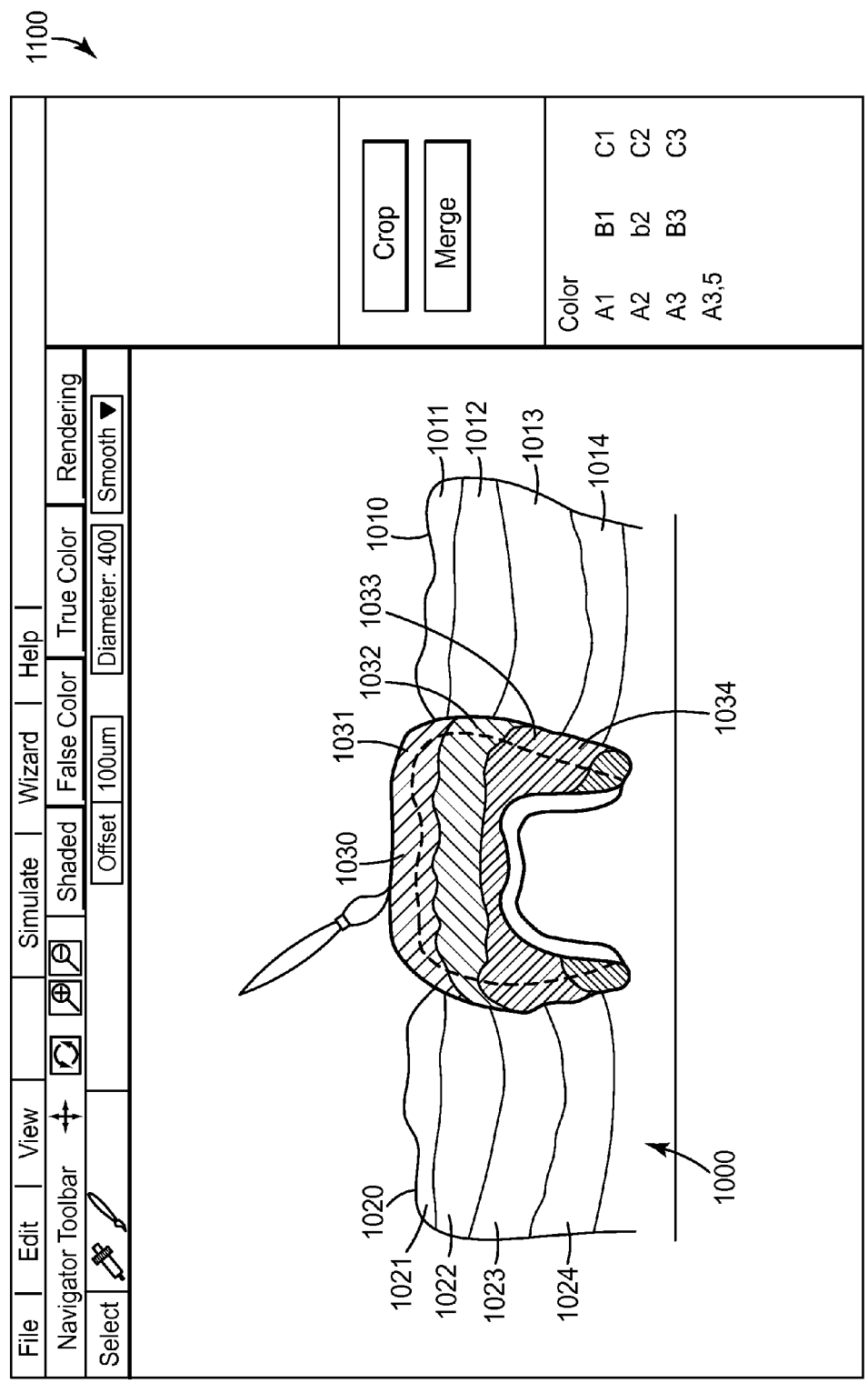
FIG. 5 is a view of a computer screen of a system according to an embodiment of the invention.

FIG. 5 illustrates a computer screen 1100 provided by software which may be used in combination with the present invention. The software in the example has capability of displaying a first virtual dentition model 1000. The first virtual dentition model 1000 is captured via a first optical sensor, for example by one of the exemplary devices disclosed herein. The first virtual dentition model 1000 shown represents portions of a first tooth 1010 and a second tooth 1020 of a patient's dentition. Although only schematically illustrated, the first virtual dentition model 1000 in the example is displayed in the form of a three-dimensional model on the computer screen 1100. The software may store the first virtual dentition model 1000 in the form of coordinates in a three-dimensional, for example Cartesian coordinate system. However the skilled person will recognize different mathematical formats to define a three-dimensional surface relative to a coordinate system, including different coordinate systems for such formats.

Further the first virtual dentition model 1000 represents different tooth colors 1011, 1012, 1013 and 1014 of the first tooth 1010 and different tooth colors 1021, 1022, 1023 and 1024 on a second tooth 1020. More or less colors may be provided as appropriate. The colors are measured at locations of the patient's tooth which correspond to the locations in the first virtual dentition model 1000. Due to the independent capturing of the shape and the measuring of the colors, both the shape information and the color information are relatively accurate. In one embodiment the shape of the patient's dentition may further be additionally extra-orally captured, for example scanned from a replica of the patient's dentition and matched with the intra-orally captured shape to maximize the accuracy of the shape information. Such a replica may be obtained for example by a dental impression which is used to make a plaster model. Scanning of a plaster model may be performed using an available dental scanner at relatively high precision. This is because, other than natural teeth, the surface of the plaster model typically exhibits a generally uniform color, translucency and reflectivity, which facilitates precise scanning. In addition such scanning is typically performed under predetermined lighting conditions, which further helps precise scanning. For example the intra-orally captured shape may be predominantly used to determine a reference position of the patient's dentition relative to a coordinate system and the extra-orally captured shape may be used to replace or correct the intra-orally captured shape at the same reference position.

The software may further have functions for designing a dental restoration 1030, for example Computer Aided Design (CAD) functions. The software thus preferably allows the virtual design of the shape of the dental restoration 1030, and further preferably has functionality to assign different portions of the virtual dental restoration 1030 different colors 1031, 1032, 1033, 1034. The software may further allow a user to select a color for the dental restoration in accordance with the color of one or both of the adjacent first and second teeth 1010, 1020. For example the software may allow a user to pick a color assigned to the first or second tooth 1010, 1020 and assign that color to a portion of the dental restoration, for example to pick color 1012 of the first tooth 1010 and assign the color 1032 of the dental restoration the picked color. Further optional functions of such software are described in co-pending patent application, international application number: PCT/US2012/068724 which is incorporated herein by reference.

Once the dental restoration is designed in shape and color the shape and color information are preferably transmitted to a build-up device which is adapted to build up the dental restoration from an appropriate material, for example a ceramic or glass-ceramic powder material which is subsequently sintered. Such a device is for example disclosed in WO 2012/078533 which is incorporated herein by reference.

The invention claimed is:

1. A method of capturing data from a patient's dentition, comprising the steps of:
    positioning a first optical sensor relative to patient's dentition;
    capturing via the first optical sensor at least a portion of the shape of a tooth in the patient's dentition and based thereon providing a first virtual dentition model representing that shape in a three-dimensional coordinate system,
    independent from capturing the shape, measuring a first color at a first location on the tooth portion;
    providing a correlation between the first location of the first color and a coordinate in the first virtual dentition model;
    providing a second virtual dentition model of a dental restoration;
    matching the first and second virtual dentition model to provide a resulting virtual dentition model; and
    assigning the resulting virtual restoration model the first color or a color based on the first color.

2. The method of claim 1, further comprising the step of positioning a second optical sensor relative to patient's dentition, wherein measuring of the first color is performed via the second optical sensor.

3. The method of claim 2, wherein positioning of the first sensor and the second sensor is performed simultaneously.

4. The method of claim 1, wherein the capturing of the shape involves processing of a series of bit map images and creating the first virtual dentition model based on the images.

5. The method of claim 4, further comprising the step of associating the first color with the at least one coordinate in the first virtual dentition model based on the correlation between the first location of the first color and the coordinate in the first virtual dentition model.

6. The method of claim 1, further comprising the steps of:
    measuring a second color at a second location on the same tooth or a further tooth in the patient's dentition, the second location being different from the first location;
    in case of measuring the second color on the further tooth, capturing via the first optical sensor at least a portion of the shape of that further tooth and based thereon updating the first virtual dentition model by the shape of the further tooth; and
    providing a correlation between the second location of the second color and a further coordinate in the (updated) first virtual dentition model.

7. The method of claim 1, further comprising the step of matching at least the first color with a standard color from a standard color scheme.

8. The method of claim 1, further comprising the step of visualizing the first virtual dentition model including information about the first color in geometric relation to the first virtual dentition model.

9. The method of claim 8, further comprising the step of providing within the first virtual dentition model a false or true color visualization of the first color in appropriate positional relationship with the coordinate correlated with the first location.

10. The method of claim 1, further comprising the step of manufacturing a dental restoration using a coloring enabled process and thereby providing the dental restoration with a color based on the first color.

11. A system for capturing data from a patient's dentition, comprising:
    a first optical sensor;
    the system being adapted by aid of the first optical sensor to capture the shape of a tooth portion of the patient's dentition in the form of a first virtual dentition model representing that shape in a three-dimensional coordinate system,
    the system comprising a second optical sensor being adapted to measure a first color at a first location on the tooth portion independently from capturing the shape;
    wherein the system is further adapted for providing a correlation between the first location of the first color and a coordinate in the first virtual dentition model;
    wherein the system is further adapted for providing a resulting virtual dentition model by matching the first virtual dentition model and a second virtual dentition model of a dental restoration, and
    wherein the system is further adapted to assign the resulting virtual restoration model the first color or a color based on the first color.

12. The system of claim 11, wherein the first optical sensor comprises a plurality of CCD photo sensors, and wherein the second optical sensor forms at least part of a spectrometer.

13. The system of claim 11, wherein the first optical sensor and the second optical sensor are arranged in a handpiece at a fixed geometric relationship to each other.

14. The system of claim 11, further comprising a computer configured to, upon positioning the first optical sensor relative to patient's dentition:
    capture via the first optical sensor the tooth portion;
    provide, based on the tooth portion, a first virtual dentition model representing that shape in a three-dimensional coordinate system;
    measure, independent from capturing the shape, the first color at the first location on the tooth portion; and
    provide the correlation between the first location of the first color and the coordinate in the first virtual dentition model.

* * * * *